(12) United States Patent
Yamashita et al.

(10) Patent No.: US 9,480,538 B2
(45) Date of Patent: Nov. 1, 2016

(54) DENTAL TREATING APPARATUS

(71) Applicant: J. Morita Manufacturing Corporation, Kyoto (JP)

(72) Inventors: Seiichiro Yamashita, Kyoto (JP); Kyoshi Tokunaga, Kyoto (JP); Naoki Katsuda, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 0 days.

(21) Appl. No.: 13/775,821

(22) Filed: Feb. 25, 2013

(65) Prior Publication Data
US 2013/0224678 A1    Aug. 29, 2013

(30) Foreign Application Priority Data

Feb. 24, 2012 (JP) ................................ 2012-038975

(51) Int. Cl.
| | |
|---|---|
| *A61C 1/00* | (2006.01) |
| *A61C 1/02* | (2006.01) |
| *A61C 19/04* | (2006.01) |
| *A61C 1/10* | (2006.01) |

(52) U.S. Cl.
CPC ............... *A61C 1/003* (2013.01); *A61C 1/02* (2013.01); *A61C 19/041* (2013.01); *A61C 2204/005* (2013.01)

(58) Field of Classification Search
CPC   A61C 1/02; A61C 19/041; A61C 2204/005; A61C 1/003
USPC ........................................ 433/27, 98–99, 114
See application file for complete search history.

(56) References Cited

U.S. PATENT DOCUMENTS

| 4,900,252 A | 2/1990 | Liefke et al. |
| 5,980,248 A | 11/1999 | Kusakabe et al. |
| 7,476,101 B2 * | 1/2009 | McPherson et al. ............ 433/75 |

(Continued)

FOREIGN PATENT DOCUMENTS

| JP | 2592423 B2 | 3/1997 |
| JP | 3264607 B2 | 3/2002 |

(Continued)

OTHER PUBLICATIONS

English abstract of Japanese Publication No. 3264607 published on Mar. 11, 2002, Espacenet database, 1 page.

(Continued)

*Primary Examiner* — Cris L Rodriguez
*Assistant Examiner* — Hao D Mai
(74) *Attorney, Agent, or Firm* — Osha Liang LLP (57) ABSTRACT

The present invention is directed to a dental treating apparatus including: a hand piece; a power source (micro motor); a driving unit (motor driver); and a controller. The driving unit drives the cutting tool so as to be switchable between first driving in which the cutting tool is driven clockwise and second driving in which the cutting tool is driven counterclockwise. When a rotation direction in which the cutting tool cuts an object to be cut is defined as normal rotation and a rotation direction opposite to the normal rotation is defined as reverse rotation, the controller sets the first driving as driving for the normal rotation when a first cutting tool rotated clockwise is held on the head unit, and sets the second driving as the driving for the normal rotation when a second cutting tool rotated counterclockwise is held on the head unit.

12 Claims, 6 Drawing Sheets

(56) References Cited

U.S. PATENT DOCUMENTS

| | | |
|---|---|---|
| 2002/0182564 A1 | 12/2002 | Katsuda et al. |
| 2003/0236669 A1 | 12/2003 | Lewallen |
| 2005/0042572 A1 | 2/2005 | Katsuda et al. |
| 2008/0254404 A1 | 10/2008 | Heraud |
| 2008/0293008 A1* | 11/2008 | Regere ................ A61C 1/0015 433/119 |
| 2010/0109644 A1 | 5/2010 | Pruckner et al. |
| 2010/0161955 A1 | 6/2010 | Helfenbein et al. |
| 2015/0105916 A1 | 4/2015 | Helfenbein et al. |

FOREIGN PATENT DOCUMENTS

| | | |
|---|---|---|
| JP | 2003-504113 A | 2/2003 |
| JP | 3615209 B2 | 2/2005 |
| JP | 3676753 B2 | 7/2005 |
| JP | 2010-148878 A | 7/2010 |
| WO | 01/03601 A1 | 1/2001 |
| WO | 2010/066337 A1 | 6/2010 |

OTHER PUBLICATIONS

English abstract of Japanese Publication No. 3676753 published on Jul. 27, 2005, Espacenet database, 1 page.

English abstract of Japanese Publication No. 3615209 published on Feb. 2, 2005, Espacenet database, 1 page.

Office Action issued in counterpart German Patent Application No. 10 2013 002 510.9 dated Feb. 20, 2014 (8 pages).

Decision to Grant Patent issued Sep. 29, 2015, in related Japanese Patent Application No. 2012-038975 (with translation) (6 pages).

Office Action issued Apr. 7, 2015 in corresponding Japanese Patent Application No. 2012-038975 (with translation) (7 pages).

* cited by examiner

|  | NORMAL ROTATION | REVERSE ROTATION |
|---|---|---|
| SETTING FOR CLOCKWISE ROTATION | CLOCKWISE ROTATION | COUNTERCLOCKWISE ROTATION |
| SETTING FOR COUNTERCLOCKWISE ROTATION | COUNTERCLOCKWISE ROTATION | CLOCKWISE ROTATION |

DENTAL TREATING APPARATUS

BACKGROUND OF THE INVENTION

1. Field of the Invention

The present invention relates to a dental treating apparatus with a hand piece, more specifically, to a dental treating apparatus that causes a cutting tool for cutting and enlarging an inner wall of a root canal of a tooth to be driven.

2. Description of the Background Art

As for a dental treating apparatus with a hand piece, there is, for example, an apparatus for providing treatment by attaching a cutting tool to a head unit of a hand piece and driving the cutting tool to cut and enlarge a root canal of a tooth. U.S. Pat. No. 3,264,607 (PTL 1), U.S. Pat. No. 3,676,753 (PTL 2) and U.S. Pat. No. 3,615,209 (PTL 3) disclose various types of driving control in order to, for example, prevent breakage due to a load applied to the cutting tool when the dental treating apparatus causes the cutting tool to be driven to cut and enlarge the root canal of the tooth.

A dental treating apparatus disclosed in PTL 1 includes detecting means for detecting a load applied to a cutting tool, and control means for reversely rotating a cutting tool driving motor when the detected load reaches a preset reference.

A dental treating apparatus disclosed in PTL 2 includes driving means for driving a cutting tool, load detecting means for detecting a load applied to the cutting tool, root canal length measuring means for measuring a root canal length by using the cutting tool, reference load setting means for arbitrarily presetting a reference load, and control means for controlling the driving means. When the load detected by the load detecting means exceeds the reference load, the control means controls the driving means by any one of the operations of stopping driving of the cutting tool, reducing an amount of driving, reversing rotation, and repeating normal rotation and reverse rotation, such that the load applied to the cutting tool is reduced. Furthermore, based on a value of the root canal length measured by the root canal length measuring means, the control means controls the driving means such that the amount of driving the cutting tool becomes smaller as a distance from the cutting tool to a root apex becomes shorter.

A dental treating apparatus disclosed in PTL 3 includes driving means for driving a cutting tool, root canal length measuring means for measuring a root canal length, and control means for controlling the driving means such that the driving force of the cutting tool changes in accordance with a value of the root canal length measured by the root canal length measuring means. The control means includes number-of-rotations control means for controlling the number of rotations of the cutting tool. Based on the value of the root canal length measured by the root canal length measuring means, the number-of-rotations control means controls the driving means such that the number of rotations of the cutting tool becomes smaller as a distance from the cutting tool to a root apex becomes shorter.

The cutting tool used for the dental treating apparatus is broadly divided into a clockwise-rotating cutting tool having a blade formed such that the cutting tool can be rotated clockwise as directed toward a tip end to cut an object to be cut, and a counterclockwise-rotating cutting tool having a blade formed such that the cutting tool can be rotated counterclockwise as directed toward the tip end to cut the object to be cut.

The cutting tool is, however, in the shape of a needle having a length of approximately several tens of millimeters, and at first glance of the shape of the blade formed on a surface, it is difficult for a user to distinguish between the clockwise-rotating cutting tool and the counterclockwise-rotating cutting tool.

The clockwise-rotating cutting tool and the counterclockwise-rotating cutting tool can be both held on the head unit of the hand piece. Therefore, in a clinical scene where the dental treating apparatus is used, the clockwise-rotating cutting tool may be used or the counterclockwise-rotating cutting tool may be used, and thus, the user must identify whether the cutting tool held on the head unit of the hand piece is the clockwise-rotating cutting tool or the counterclockwise-rotating cutting tool. Unless the user drives the cutting tool at a rotation appropriate for the cutting tool held on the head unit, the user cannot properly cut the root canal of the tooth.

Furthermore, when various types of driving control disclosed in PTLs 1 to 3 are performed in the dental treating apparatus, false driving control is performed and treatment cannot be provided safely unless the user checks whether the driving control is driving control appropriate for the clockwise-rotating cutting tool or driving control appropriate for the counterclockwise-rotating cutting tool.

SUMMARY OF THE INVENTION

The present invention provides a dental treating apparatus that can safely and properly cut an object to be cut, regardless of the shape of a cutting tool held on a head unit.

A dental treating apparatus according to the present invention includes: a hand piece; a power source; a driving unit; and a controller. The hand piece drivably holds a cutting tool on a head unit. The power source drives the cutting tool. The driving unit drives the cutting tool so as to be switchable between first driving in which the cutting tool is driven clockwise as directed toward a tip end of the cutting tool and second driving in which the cutting tool is driven counterclockwise as directed toward the tip end of the cutting tool. When a rotation direction in which the cutting tool cuts an object to be cut is defined as normal rotation and a rotation direction opposite to the normal rotation is defined as reverse rotation, the controller sets either the first driving or the second driving as driving for the normal rotation, based on the cutting tool held on the head unit. The controller sets the first driving as the driving for the normal rotation when a first cutting tool of the cutting tool rotated clockwise as directed toward the tip end to cut the object to be cut is held on the head unit, and sets the second driving as the driving for the normal rotation when a second cutting tool of the cutting tool rotated counterclockwise as directed toward the tip end to cut the object to be cut is held on the head unit.

In the dental treating apparatus according to the present invention, the controller sets the first driving as the normal rotation driving when the first cutting tool, of the cutting tool, is held on the head unit, and sets the second driving as the normal rotation driving when the second cutting tool is held on the head unit. Therefore, in the dental treating apparatus according to the present invention, the user can cut the object to be cut simply by rotating the cutting tool normally, without being aware of whether the cutting tool held on the head unit is the first cutting tool or the second cutting tool. Thus, in the dental treating apparatus according to the present invention, user's misconception and operation mistake can be prevented even in the environment where the first cutting tool may be used or the second cutting tool may be used.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Hereinafter, embodiments of the present invention are described with reference to the drawings.

First Embodiment

A dental treating apparatus according to a first embodiment of the present invention is a root canal treating device including a root canal enlarging and root canal length measuring system into which a dental hand piece for treatment on a root canal is incorporated. The dental treating apparatus according to the present invention is, however, not limited to the root canal treating device, and can be applied to a dental treating apparatus with a similar configuration.

Figure 1:
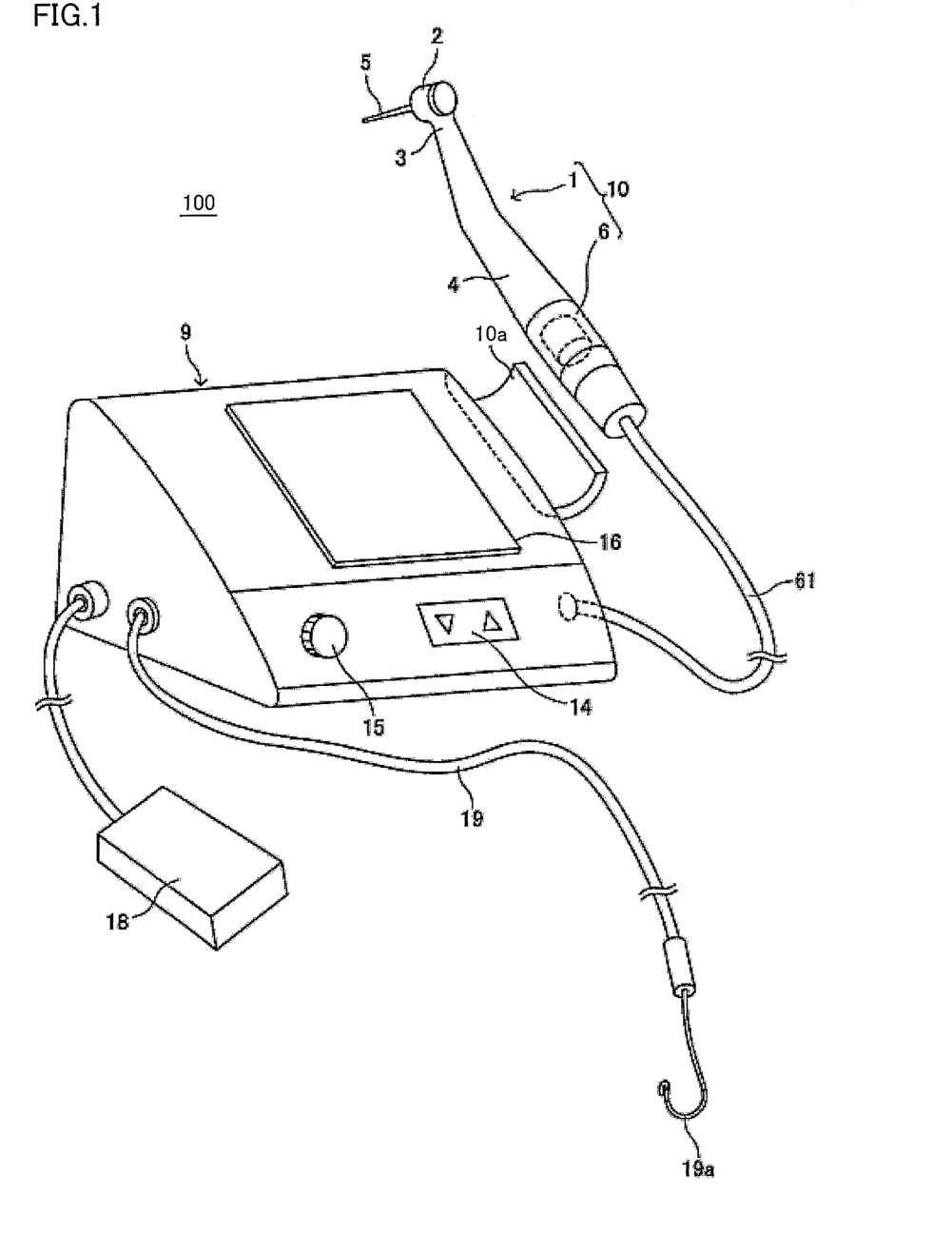
FIG. 1 is a schematic diagram showing an appearance of a configuration of a root canal treating device according to a first embodiment of the present invention.
Figure 2:
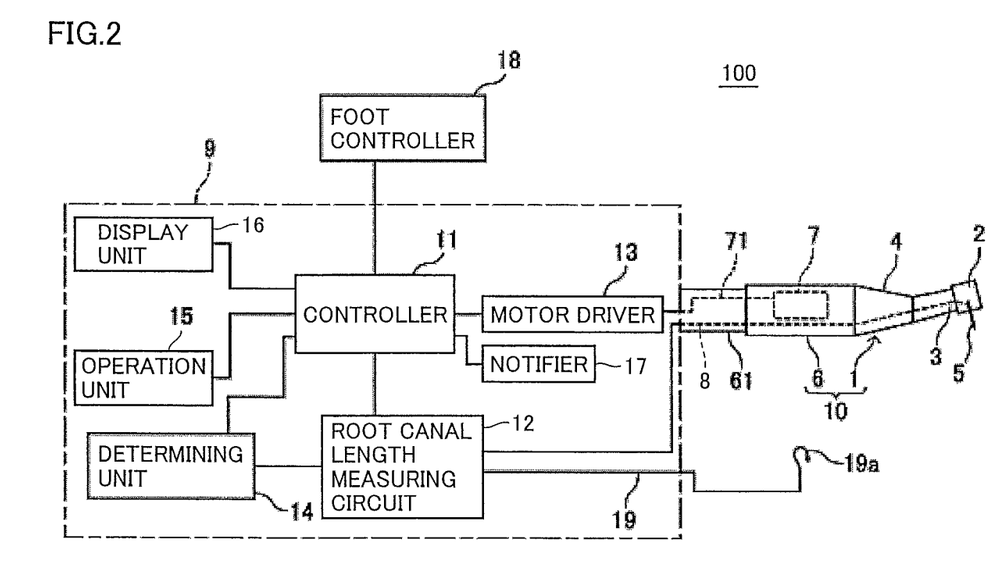
FIG. 2 is a block diagram showing a configuration of functions of the root canal treating device according to the first embodiment of the present invention.

FIG. 1 is a schematic diagram showing an appearance of a configuration of the root canal treating device according to the first embodiment of the present invention. FIG. 2 is a block diagram showing a configuration of functions of the root canal treating device according to the first embodiment of the present invention. A root canal treating device 100 as shown in FIG. 1 includes a hand piece 1, a motor unit 6 and a control box 9 for treating dental root canal.

Hand piece 1 for treating the dental root canal includes a head unit 2, a neck unit 3 with a small diameter connected to head unit 2, and a grip 4 connected to neck unit 3 and gripped by a hand or fingers. Further, to a base unit of grip 4, motor unit 6 is detachably connected for rotating and driving a cutting tool 5 to be held on head unit 2. A dental instrument 10 is configured with hand piece 1 and motor unit 6 coupled to each other.

As shown in FIG. 2, a micro motor 7 is embedded in motor unit 6 that is connected to control box 9 through a hose 61 containing therein a power supply lead 71 for supplying power to micro motor 7, a signal lead 8 for transmitting a signal to a root canal length measuring circuit 12 to be described below, and the like. Here, signal lead 8 is a part of a conductive body for transmitting an electric signal, signal lead 8 being electrically connected to cutting tool 5 through motor unit 6 and hand piece 1. It is also noted that cutting tool 5 is one of electrodes of root canal length measuring circuit 12.

Control box 9 includes a controller 11, root canal length measuring circuit 12, a motor driver 13, a determining unit 14, an operation unit 15, a display unit 16, a notifier 17, and the like. As shown in FIG. 1, it should be noted that control box 9 is provided with a holder 10a holding instrument 10 when instrument 10 is not used, at a lateral part of a body. Also, a foot controller 18 is connected to control box 9. Further, control box 9 is connected to a lead 19 through which control box 9 is electrically connected to root canal length measuring circuit 12. Lead 19 may be in a form that is bifurcated at an intermediate portion of hose 61. A mouth electrode 19a hung on a lip of a patient is attached to a tip end of lead 19 in an electrically conductive state. It should be noted that mouth electrode 19a is the other one of the electrodes of root canal length measuring circuit 12.

A primary part of controller 11 for controlling the whole system for enlarging the root canal and measuring the root canal length is configured by a microcomputer. Root canal length measuring circuit 12, motor driver 13, determining unit 14, operation unit 15, display unit 16, notifier 17, and foot controller 18 are connected to controller 11. Controller 11 sets, as normal rotation driving, either clockwise rotation driving (first driving) in which cutting tool 5 is driven clockwise as directed toward a tip end of cutting tool 5 or counterclockwise rotation driving (second driving) in which cutting tool 5 is driven counterclockwise as directed toward the tip end of cutting tool 5. The contents of this setting are stored in controller 11 or a memory in control box 9, although not shown. Here, the normal rotation refers to rotation in a rotation direction in which cutting tool 5 cuts an object to be cut, and the reverse rotation refers to rotation in a rotation direction opposite to the normal rotation.

Root canal length measuring circuit 12 configures a closed circuit with cutting tool 5 inserted in the root canal of the tooth as one electrode and mouth electrode 19a hung on the lip of the patient as the other electrode. Root canal length measuring circuit 12 can measure a distance from an apical position of the tooth to a tip end of cutting tool 5 by applying voltage between cutting tool 5 and mouth electrode 19a and measuring impedance between cutting tool 5 and mouth electrode 19a. An amount of insertion of cutting tool 5, that is, a distance from an opening of the root canal to the tip end of cutting tool 5, when root canal length measuring circuit 12 detects that the tip end of cutting tool 5 has reached the apical position can be defined as the root canal length. It should be noted that a method for electrically measuring the root canal length by measuring the impedance between cutting tool 5 and mouth electrode 19a is publicly known and all publicly-known methods for electrically measuring the root canal length can be applied to root canal treating device 100 according to the first embodiment of the present invention.

Motor driver 13 is connected to micro motor 7 via power supply lead 71 and controls the power supplied to micro motor 7 based on a control signal from controller 11. Motor driver 13 can drive cutting tool 5 so as to be switchable between the clockwise rotation driving and the counterclockwise rotation driving. Motor driver 13 can also control the rotation direction, the number of rotations, the rotation angle and the like of micro motor 7, namely the rotation direction, the number of rotations, the rotation angle and the like of cutting tool 5 by controlling the power supplied to micro motor 7.

Based on information obtained from cutting tool 5, determining unit 14 determines whether cutting tool 5 held on head unit 2 is the clockwise-rotating cutting tool (first cutting tool) having the blade formed such that the cutting tool can be rotated clockwise as directed toward the tip end to cut the object to be cut or the counterclockwise-rotating cutting tool (second cutting tool) having the blade formed such that the cutting tool can be rotated counterclockwise as directed toward the tip end to cut the object to be cut. The information obtained from cutting tool 5 includes driving information indicating a driving state of cutting tool 5, identification information for identifying whether cutting tool 5 is the clockwise-rotating cutting tool or the counterclockwise-rotating cutting tool, and the like. Specific examples of the information obtained from cutting tool 5 are provided and described in the embodiments below, although the present invention is not limited thereto.

It should be noted that the root canal treating device according to the present invention does not always need to include determining unit 14. Based on the shape of the blade of cutting tool 5 (information obtained from cutting tool 5), the user may identify whether cutting tool 5 is the clockwise-rotating cutting tool or the counterclockwise-rotating cutting tool, and operation unit 15 may set the normal rotation driving.

Operation unit 15 can select whether or not the normal rotation driving is automatically set as well as whether or not the root canal length is measured. Operation unit 15 can also manually switch between the normal rotation driving and the reverse rotation driving.

Display unit 16 displays a position of the tip end of cutting tool 5 in the root canal and the rotation direction, the number of rotations, the rotation angle and the like of cutting tool 5 as described below. Also, display unit 16 can display information for notifier 17 to notify a user.

Notifier 17 notifies the user by light, sound, vibration, and the like of the driving state of cutting tool 5 that is being executed by controller 11. Specifically, notifier 17 includes an LED (Light Emitting Diode), a speaker, an oscillator, and the like according to the need to notify the user of the driving state of cutting tool 5, and colors of the light emitted from the LED change or sounds outputted from the speaker change based on whether the normal rotation driving is being executed or the reverse rotation driving is being executed. Also, notifier 17 need not include the LED, the speaker, the oscillator and the like separately if display unit 16 can display the driving state of cutting tool 5 for the user. Notifier 17 may also notify the user of the information about whether cutting tool 5 held on head unit 2 is the clockwise-rotating cutting tool or the counterclockwise-rotating cutting tool.

Foot controller 18 is an operation unit for performing driving control on cutting tool 5 by micro motor 7 by a stepping operation. It should be noted that the driving control on cutting tool 5 by micro motor 7 is not limited to foot controller 18, namely, an operation switch (not shown) is provided in grip 4 of hand piece 1 to perform the driving control on cutting tool 5 by this operation switch and foot controller 18. Also, for example, in a state where the stepping operation via foot controller 18 is performed, the rotation of cutting tool 5 may be started by detecting, using root canal length measuring circuit 12, that cutting tool 5 is inserted into the root canal.

It should be noted that a configuration is disclosed in that control box 9 of root canal treating device 100 is put on a tray table or a side table installed on a lateral part of a dental treatment table and used. The present invention is, however, not limited to such a configuration but can include a configuration in that control box 9 is incorporated into the tray table or the side table.

Figure 3:
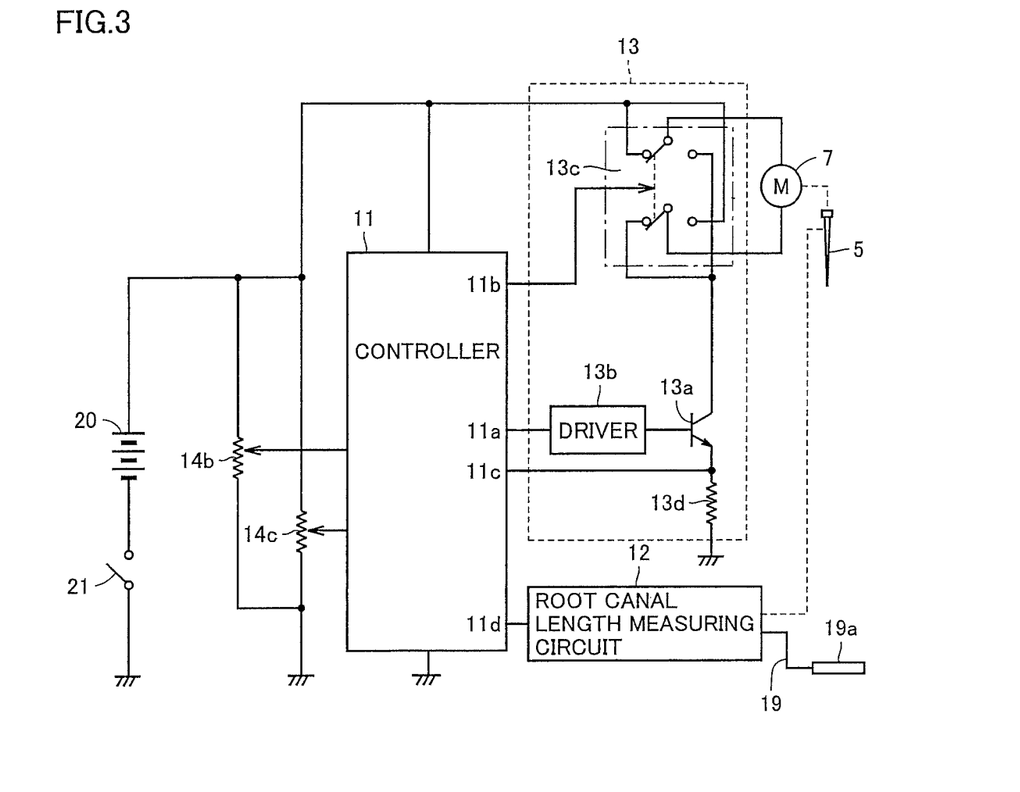
FIG. 3 is a circuit diagram showing a circuit configuration of the root canal treating device according to the first embodiment of the present invention.

Next, a configuration of root canal treating device 100 for performing the driving control on cutting tool 5 is described in more details. FIG. 3 is a circuit diagram showing a circuit configuration of root canal treating device 100 according to the first embodiment of the present invention. In root canal treating device 100 shown in FIG. 3, components of micro motor 7, controller 11, root canal length measuring circuit 12, and motor driver 13 that are involved in the driving control on cutting tool 5 are illustrated.

Furthermore, motor driver 13 includes a transistor switch 13*a*, a transistor driver circuit 13*b*, a rotation direction switching switch 13*c*, and a resistor 13*d* for load detection. Controller 11 is connected to a variable resistor 14*b* for setting a duty, a variable resistor 14*c* for setting the apical position, a main power supply 20 for root canal treating device 100, and a main switch 21. Cutting tool 5 is held on micro motor 7 via an appropriate gear mechanism and the like, although not shown.

Transistor driver circuit 13*b* operates in response to a control signal outputted from a port 11*a* of controller 11, and controls ON/OFF of transistor switch 13*a* and drives micro motor 7. Micro motor 7 rotates clockwise or counterclockwise in accordance with a state of rotation direction switching switch 13*c*. When the control signal outputted from port 11*a* of controller 11 has, for example, a pulse waveform repeated in a certain cycle, a width of the pulse, that is, a duty ratio is adjusted by variable resistor 14*b* for setting a duty. In accordance with this duty ratio, micro motor 7 rotates and drives cutting tool 5.

In response to a control signal outputted from a port 11*b* of controller 11, rotation direction switching switch 13*c* switches between rotating clockwise and driving cutting tool 5 and rotating counterclockwise and driving cutting tool 5. Controller 11 receives a resistance value of resistor 13*d* for load detection at a port 11*c* and detects a load applied to cutting tool 5. Furthermore, controller 11 receives the root canal length measured by root canal length measuring circuit 12 at a port 11*d*. With the configuration described above, micro motor 7 and cutting tool 5 are rotated clockwise or counterclockwise based on the set normal rotation or reverse rotation direction.

Next, a relationship between the shape of cutting tool 5 and the driving control is described.

Cutting tool 5 includes the clockwise-rotating cutting tool and the counterclockwise-rotating cutting tool. The user can freely change the clockwise-rotating cutting tool and the counterclockwise-rotating cutting tool. Therefore, in a clinical scene, the clockwise-rotating cutting tool may be used or the counterclockwise-rotating cutting tool may be used, and thus, during treatment, the user must identify whether cutting tool 5 is the clockwise-rotating cutting tool or the counterclockwise-rotating cutting tool and select appropriate driving corresponding to the shape of cutting tool 5 (e.g., the clockwise rotation driving in the case of the clockwise-rotating cutting tool).

Figure 4A:
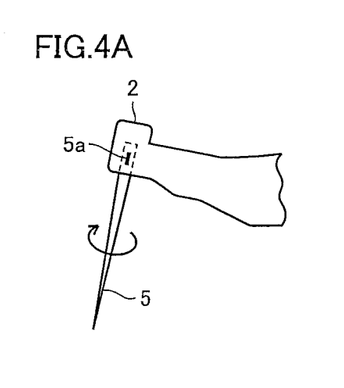
FIG. 4A is a schematic diagram showing a rotation direction of a cutting tool in the case of clockwise rotation driving.
Figure 4B:
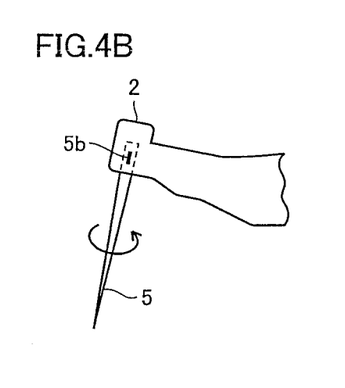
FIG. 4B is a schematic diagram showing a rotation direction of the cutting tool in the case of counterclockwise rotation driving.

FIGS. 4A and 4B are schematic diagrams showing rotation directions of cutting tool 5 in the case of the clockwise rotation driving and in the case of the counterclockwise rotation driving, respectively. FIG. 4A shows the rotation direction of cutting tool 5 in the case of the clockwise rotation driving, and FIG. 4B shows the rotation direction of cutting tool 5 in the case of the counterclockwise rotation driving. When the clockwise-rotating cutting tool is held on head unit 2, the clockwise rotation driving shown in FIG. 4A is executed, and thereby root canal treating device 100 can appropriately cut an inner wall of the root canal of the tooth. On the other hand, when the counterclockwise-rotating cutting tool is held on head unit 2, the counterclockwise rotation driving shown in FIG. 4B is executed, and thereby root canal treating device 100 can appropriately cut the inner wall of the root canal of the tooth.

Figure 5:
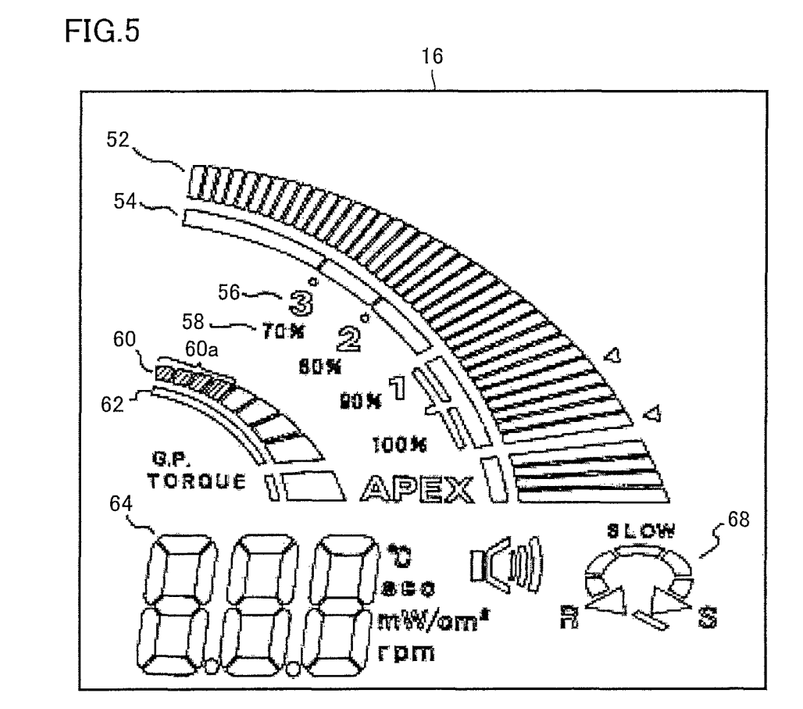
FIG. 5 is a diagram showing a display example of a liquid crystal display panel of a display unit shown in FIG. 1.

Next, display of a liquid crystal display panel of display unit 16 shown in FIG. 1 is described. FIG. 5 is a diagram showing a display example of the liquid crystal display panel of display unit 16 shown in FIG. 1.

Display unit 16 shown in FIG. 5 is the liquid crystal display panel, and is provided with a dot display unit 52 including many elements for displaying the measured root canal length in detail, a zone display unit 54 for zoning and displaying the root canal length in a stepwise manner, a boundary display unit 56 for displaying a boundary of each zone, and an arrival rate display unit 58 for displaying a rate of arrival at the root apex.

Dot display unit 52 is configured such that the elements are sequentially displayed from the top to the bottom as the tip end of cutting tool 5 comes closer to the root apex. A position of the gauge "APEX" shows a position of the root apex, and arrival of the elements at this gauge means that the tip end of cutting tool 5 has nearly arrived at the position of the root apex.

Display unit 16 is also provided with a dot display unit 60 including many elements for displaying the load detected by resistor 13d for load detection, and a zone display unit 62 for zoning and displaying the load in a stepwise manner. Dot display unit 60 is configured such that the elements are sequentially displayed from the top to the bottom as the load detected by resistor 13d for load detection becomes larger.

For example, the load applied to cutting tool 5 when cutting tool 5 is cutting the tooth is displayed on dot display unit 60 by diagonally shaded elements 60a. In order to prevent frequent switching of displays, dot display unit 60 may have a peak hold function to display, for a certain time period, a maximum value of the load detected within a prescribed time period.

Display unit 16 is further provided with a numerical value display unit 64 for numerically displaying the number of rotations of cutting tool 5 and the load applied to cutting tool 5, and a rotation display unit 68 for displaying the orientation of rotation of cutting tool 5 (normal rotation S, reverse rotation R) and the number of rotations of cutting tool 5. It should be noted that normal rotation S and reverse rotation R are displayed as shown in FIG. 5 when the clockwise-rotating cutting tool is held on head unit 2. When the counterclockwise-rotating cutting tool is held on head unit 2, the positions of normal rotation S and reverse rotation R are reversed.

Next, description is given to a configuration in which root canal treating device 100 according to the first embodiment sets the normal rotation driving based on the information obtained from cutting tool 5. First, a case is shown in which the identification information for identifying the cutting tool is used as the information obtained from cutting tool 5. Specifically, a case is described in which cutting tool 5 has an identification tag 5a or 5b for identifying whether cutting tool 5 is the clockwise-rotating cutting tool or the counterclockwise-rotating cutting tool as shown in FIGS. 4A and 4B.

Identification tag 5a is an IC tag, for example, and information such as a serial number and the information that cutting tool 5 has the shape of the clockwise-rotating cutting tool is written on identification tag 5a. Similarly, identification tag 5b is also an IC tag, for example, and information such as a serial number and the information that cutting tool 5 has the shape of the counterclockwise-rotating cutting tool is written on identification tag 5b. When cutting tool 5 having identification tag 5a or 5b is held on head unit 2 as shown in FIGS. 4A and 4B, an IC tag reading sensor (not shown) provided preliminarily in head unit 2 reads the information about the shape of cutting tool 5 from identification tag 5a or 5b of cutting tool 5. The IC tag reading sensor outputs the read information about the shape of cutting tool 5 to determining unit 14 via controller 11. Then, determining unit 14 determines whether cutting tool 5 held on head unit 2 is the clockwise-rotating cutting tool or the counterclockwise-rotating cutting tool.

When determining unit 14 determines that cutting tool 5 held on head unit 2 is the clockwise-rotating cutting tool, controller 11 sets the clockwise rotation driving as the normal rotation driving. When determining unit 14 determines that cutting tool 5 held on head unit 2 is the counterclockwise-rotating cutting tool, controller 11 sets the counterclockwise rotation driving as the normal rotation driving.

It should be noted that the identification information for identifying whether cutting tool 5 is the clockwise-rotating cutting tool or the counterclockwise-rotating cutting tool is not limited to the IC tag and may be a two-dimensional bar code, a magnetic tag and the like. Furthermore, the identification information may be a change in the shape of a unit for holding cutting tool 5 depending on whether cutting tool 5 is the clockwise-rotating cutting tool or the counterclockwise-rotating cutting tool (identification shape). For example, the holding unit has such a shape that, in the case of the clockwise-rotating cutting tool, cutting tool 5 does not come into contact with a contact point provided in head unit 2 when cutting tool 5 is held on head unit 2, and in the case of the counterclockwise-rotating cutting tool, cutting tool 5 comes into contact with the contact point provided in head unit 2 when cutting tool 5 is held on head unit 2.

Next, a case is shown in which the driving information indicating the driving state of the cutting tool is used as the information obtained from cutting tool 5. Specifically, it is identified whether held cutting tool 5 is the clockwise-rotating cutting tool or the counterclockwise-rotating cutting tool, using a difference between a load applied when cutting tool 5 held on head unit 2 is driven with the clockwise rotation driving and a load applied when cutting tool 5 held on head unit 2 is driven with the counterclockwise rotation driving.

Figure 6:
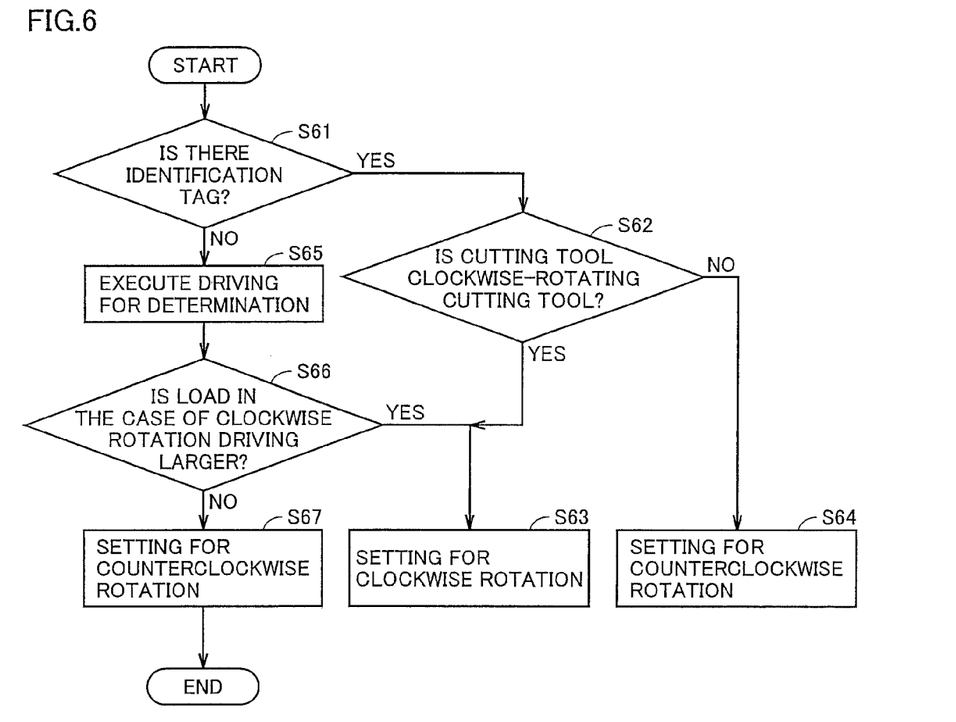
FIG. 6 is a flowchart for describing a method for setting normal rotation driving in the root canal treating device according to the first embodiment of the present invention.

FIG. 6 is a flowchart for describing a method for setting the normal rotation driving in root canal treating device 100 according to the first embodiment of the present invention. First, controller 11 determines whether cutting tool 5 has the identification tag or not (step S61). If controller 11 determines that cutting tool 5 has the identification tag (YES in step S61), determining unit 14 determines whether cutting tool 5 has the shape of the clockwise-rotating cutting tool or not, based on the identification information read from the identification tag (step S62).

If determining unit 14 determines in step S62 that cutting tool 5 has the shape of the clockwise-rotating cutting tool (YES in step S62), controller 11 sets the clockwise rotation driving as the normal rotation driving (setting for clockwise rotation) (step S63). On the other hand, if determining unit 14 determines in step S62 that cutting tool 5 has the shape of the counterclockwise-rotating cutting tool (NO in step S62), controller 11 sets the counterclockwise rotation driving as the normal rotation driving (setting for counterclockwise rotation) (step S64).

Returning to step S61, if controller 11 determines that cutting tool 5 does not have the identification tag (NO in step S61), controller 11 executes driving for determining the shape of cutting tool 5 (driving for determination) (step S65). Although the example is described in which the driving for determination is executed when cutting tool 5 does not have the identification tag, the driving for determination may be executed when cutting tool 5 has the identification tag. The driving for determination may be executed by cutting a dedicated object to be cut or by cutting the inner wall of the root canal of the tooth to be treated. When the driving for determination is executed by cutting the inner wall of the root canal of the tooth to be treated, a part of a period during which the tooth is cut, e.g., a certain period from the start of cutting, may be used for the driving for determination.

Now, description is given to a principle of identifying the shape of held cutting tool 5 by comparing the load applied when cutting tool 5 held on head unit 2 is driven with the clockwise rotation driving and the load applied when cutting tool 5 held on head unit 2 is driven with the counterclockwise rotation driving. The clockwise-rotating cutting tool has the blade formed such that the cutting tool can cut the object to be cut when driven with the clockwise rotation driving. Therefore, the load applied at the time of clockwise rotation is large and the load applied at the time of counterclockwise rotation is small. On the other hand, the counterclockwise-rotating cutting tool has the blade formed such that the cutting tool can cut the object to be cut when driven with the counterclockwise rotation driving. Therefore, the load applied at the time of counterclockwise rotation is large and the load applied at the time of clockwise rotation is small.

Therefore, when cutting tool 5 held on head unit 2 has the shape of the clockwise-rotating cutting tool, the load applied when cutting tool 5 is driven with the clockwise rotation driving is larger than the load applied when cutting tool 5 is driven with the counterclockwise rotation driving. Thus, when the load applied when cutting tool 5 is driven with the clockwise rotation driving is larger as a result of execution of the driving for determination, determining unit 14 can determine that cutting tool 5 held on head unit 2 is the clockwise-rotating cutting tool.

In contrast, when cutting tool 5 held on head unit 2 has the shape of the counterclockwise-rotating cutting tool, the load applied when cutting tool 5 is driven with the counterclockwise rotation driving is larger than the load applied when cutting tool 5 is driven with the clockwise rotation driving. Thus, when the load applied when cutting tool 5 is driven with the counterclockwise rotation driving is larger as a result of execution of the driving for determination, determining unit 14 can determine that cutting tool 5 held on head unit 2 is the counterclockwise-rotating cutting tool.

Determining unit 14 determines the shape of cutting tool 5 by determining, as a result of the driving for determination executed in step S65, whether the load applied when cutting tool 5 held on head unit 2 is driven with the clockwise rotation driving is larger than the load applied when cutting tool 5 held on head unit 2 is driven with the counterclockwise rotation driving (step S66).

If determining unit 14 determines that the load applied when cutting tool 5 is driven with the clockwise rotation driving is larger (YES in step S66), determining unit 14 determines that cutting tool 5 held on head unit 2 has the shape of the clockwise-rotating cutting tool, and controller 11 sets the clockwise rotation driving as the normal rotation driving (setting for clockwise rotation) (step S63).

On the other hand, if determining unit 14 determines that the load applied when cutting tool 5 is driven with the counterclockwise rotation driving is larger (NO in step S66), determining unit 14 determines that cutting tool 5 held on head unit 2 has the shape of the counterclockwise-rotating cutting tool, and controller 11 sets the counterclockwise rotation driving as the normal rotation driving (setting for counterclockwise rotation) (step S67).

Figure 7:
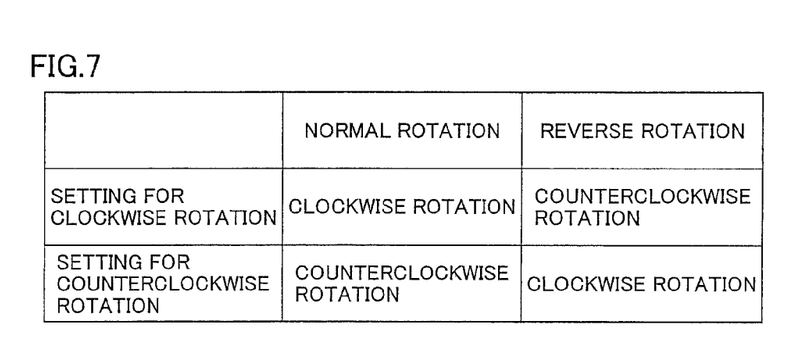
FIG. 7 is a diagram showing rotation directions of normal rotation and reverse rotation in a setting for clockwise rotation and a setting for counterclockwise rotation.

Now, description is given to rotation directions of the normal rotation and the reverse rotation in the setting when cutting tool 5 held on head unit 2 has the shape of the clockwise-rotating cutting tool (setting for clockwise rotation) as well as rotation directions of the normal rotation and the reverse rotation in the setting when cutting tool 5 held on head unit 2 has the shape of the counterclockwise-rotating cutting tool (setting for counterclockwise rotation). FIG. 7 is a diagram showing the rotation directions of the normal rotation and the reverse rotation in the setting for clockwise rotation and in the setting for counterclockwise rotation. As shown in FIG. 7, in the setting for clockwise rotation, the normal rotation is set as clockwise rotation and the reverse rotation is set as counterclockwise rotation. In the setting for counterclockwise rotation, the normal rotation is set as counterclockwise rotation and the reverse rotation is set as clockwise rotation.

The flowchart of FIG. 6 explicitly shows that the driving for determining the shape of cutting tool 5 (driving for determination) is executed in step S65. However, the user using root canal treating device 100 does not always need to be aware of this step. In other words, simply by the user starting cutting the tooth to be treated, without being aware of step S65, root canal treating device 100 may automatically execute the driving for determination, determine the shape of cutting tool 5 held on head unit 2 and set either the clockwise rotation driving or the counterclockwise rotation driving as the normal rotation driving.

As described above, in root canal treating device 100 according to the first embodiment of the present invention, controller 11 sets the clockwise rotation driving as the normal rotation driving when the clockwise-rotating cutting tool 5 is held on head unit 2, and sets the counterclockwise rotation driving as the normal rotation driving when the counterclockwise-rotating cutting tool 5 is held on head unit 2. Therefore, in root canal treating device 100 according to the first embodiment of the present invention, the user can cut the object to be cut simply by rotating cutting tool 5 normally, without being aware of whether cutting tool 5 held on head unit 2 is the clockwise-rotating cutting tool or the counterclockwise-rotating cutting tool. In other words, regardless of whether the clockwise-rotating cutting tool or the counterclockwise-rotating cutting tool is held on head unit 2, the user can cut the object to be cut, simply by performing the same operation such as the stepping operation of foot controller 18.

Thus, in root canal treating device 100 according to the first embodiment of the present invention, user's misconception and operation mistake can be prevented even in the environment where the clockwise-rotating cutting tool may be used or the counterclockwise-rotating cutting tool may be used. In addition, in root canal treating device 100 according to the first embodiment of the present invention, the driving disclosed in U.S. Pat. No. 3,676,753 (PTL 2) and the like can be applied regardless of whether cutting tool 5 held on head unit 2 is the clockwise-rotating cutting tool or the counterclockwise-rotating cutting tool.

Second Embodiment

In the first embodiment, the driving information obtained from cutting tool 5 is the load applied when cutting tool 5 held on head unit 2 is driven. In a root canal treating device according to a second embodiment, a change in the position of the tip end of cutting tool 5 when cutting tool 5 is driven to cut the object to be cut is used as the driving information obtained from cutting tool 5. It should be noted that the position of cutting tool 5 can be electrically measured by root canal length measuring circuit 12.

Since the root canal treating device according to the second embodiment has the same configuration as that of root canal treating device 100 according to the first embodiment shown in FIGS. 1 to 3, the same reference characters are assigned and detailed description will not be repeated.

Figure 8:
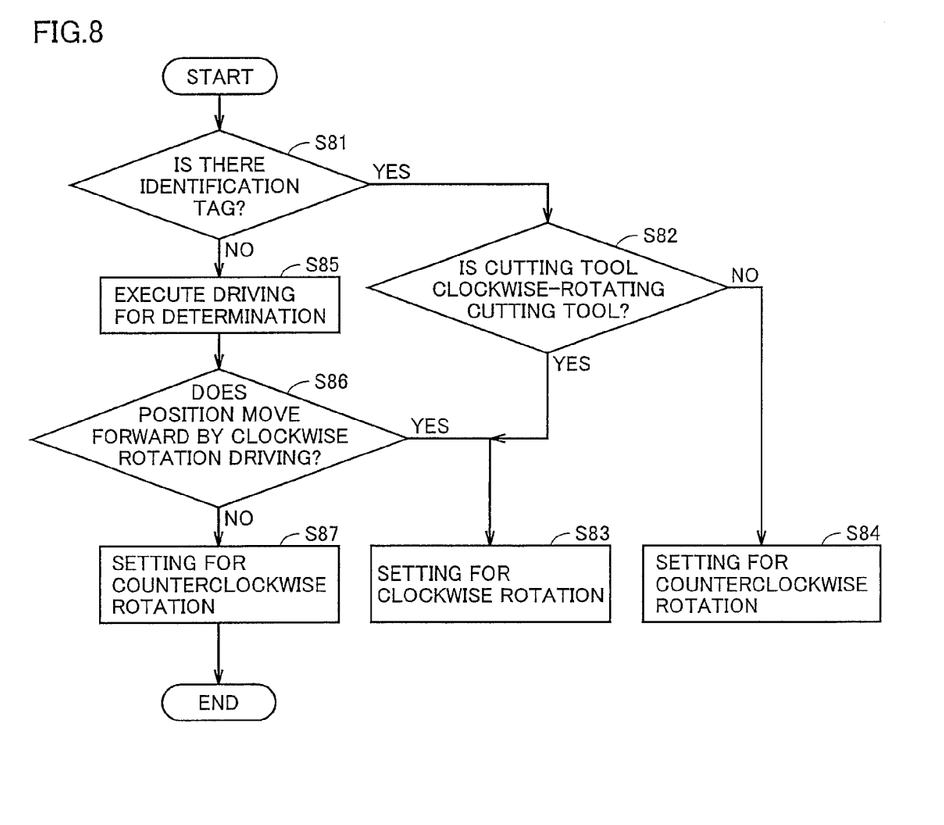
FIG. 8 is a flowchart for describing a method for setting normal rotation driving in a root canal treating device according to a second embodiment of the present invention.

FIG. 8 is a flowchart for describing a method for setting the normal rotation driving in root canal treating device 100 according to the second embodiment of the present invention. First, controller 11 determines whether cutting tool 5 has the identification tag or not (step S81). If controller 11 determines that cutting tool 5 has the identification tag (YES in step S81), determining unit 14 determines whether cutting tool 5 has the shape of the clockwise-rotating cutting tool or not, based on the identification information read from the identification tag (step S82).

If determining unit 14 determines in step S82 that cutting tool 5 has the shape of the clockwise-rotating cutting tool (YES in step S82), controller 11 sets the clockwise rotation driving as the normal rotation driving (setting for clockwise rotation) (step S83). On the other hand, if determining unit 14 determines in step S82 that cutting tool 5 has the shape of the counterclockwise-rotating cutting tool (NO in step S82), controller 11 sets the counterclockwise rotation driving as the normal rotation driving (setting for counterclockwise rotation) (step S84).

Returning to step S81, if controller 11 determines that cutting tool 5 does not have the identification tag (NO in step S81), controller 11 executes the driving for determining the shape of cutting tool 5 (driving for determination) (step S85).

Now, description is given to a principle of identifying the shape of held cutting tool 5 by using the change in the position of the tip end of cutting tool 5 when cutting tool 5 held on head unit 2 is driven to cut the object to be cut. The clockwise-rotating cutting tool has the blade formed such that the cutting tool cuts the object to be cut and moves forward in the cutting direction when rotated clockwise. Therefore, the clockwise-rotating cutting tool moves forward with respect to the cutting direction when rotated clockwise, and moves backward with respect to the cutting direction when rotated counterclockwise. On the other hand, the counterclockwise-rotating cutting tool has the blade formed such that the cutting tool cuts the object to be cut and moves forward in the cutting direction when rotated counterclockwise. Therefore, the counterclockwise-rotating cutting tool moves forward with respect to the cutting direction when rotated counterclockwise, and moves backward with respect to the cutting direction when rotated clockwise.

Therefore, when cutting tool 5 is driven with the clockwise rotation driving to cut the object to be cut in the case where cutting tool 5 held on head unit 2 has the shape of the clockwise-rotating cutting tool, the position of the tip end of cutting tool 5 moves forward with respect to the cutting direction. Thus, when the position of the tip end of cutting tool 5 moves forward with respect to the cutting direction as the driving for determination is executed and cutting tool 5 is driven with the clockwise rotation driving, determining unit 14 can determine that cutting tool 5 held on head unit 2 is the clockwise-rotating cutting tool.

In contrast, when cutting tool 5 is driven with the counterclockwise rotation driving to cut the object to be cut in the case where cutting tool 5 held on head unit 2 has the shape of the counterclockwise-rotating cutting tool, the position of the tip end of cutting tool 5 moves forward with respect to the cutting direction. Thus, when the position of the tip end of cutting tool 5 moves forward with respect to the cutting direction as the driving for determination is executed and cutting tool 5 is driven with the counterclockwise rotation driving, determining unit 14 can determine that cutting tool 5 held on head unit 2 is the counterclockwise-rotating cutting tool.

Determining unit 14 determines the shape of cutting tool 5 by determining, as a result of the driving for determination executed in step S85, whether or not the tip end of cutting tool 5 moves forward with respect to the cutting direction when cutting tool 5 held on head unit 2 is driven with the clockwise rotation driving (step S86).

If determining unit 14 determines that the position of the tip end of cutting tool 5 moves forward with respect to the cutting direction when cutting tool 5 is driven with the clockwise rotation driving (YES in step S86), determining unit 14 determines that cutting tool 5 held on head unit 2 has the shape of the clockwise-rotating cutting tool, and controller 11 sets the clockwise rotation driving as the normal rotation driving (setting for clockwise rotation) (step S83).

On the other hand, if determining unit 14 determines that the position of the tip end of cutting tool 5 moves forward with respect to the cutting direction when cutting tool 5 is driven with the counterclockwise rotation driving (NO in step S86), determining unit 14 determines that cutting tool 5 held on head unit 2 has the shape of the counterclockwise-rotating cutting tool, and controller 11 sets the counterclockwise rotation driving as the normal rotation driving (setting for counterclockwise rotation) (step S87).

As described above, in root canal treating device 100 according to the second embodiment of the present invention, determining unit 14 determines the shape of cutting tool 5 held on head unit 2, based on the change in the position of the tip end of cutting tool 5. Therefore, it is unnecessary to provide the identification tag and the like for cutting tool 5 and the present embodiment can also be applied to conventional cutting tools.

Figure 9:
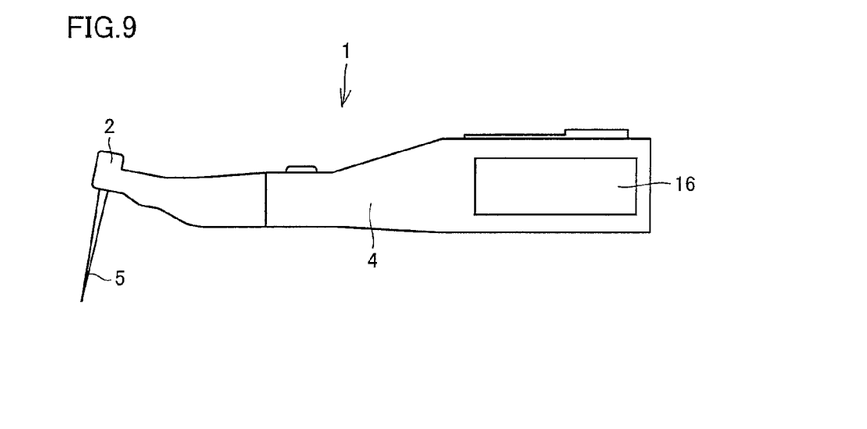
FIG. 9 is a schematic diagram showing a configuration of a cordless-type root canal treating device.

In root canal treating device 100 according to the first and second embodiments, the configuration in which hand piece 1 is coupled to control box 9 via hose 61 has been described. The present invention is not, however, limited thereto but may be configured as a cordless-type root canal treating device. FIG. 9 is a schematic diagram showing a configuration of the cordless-type root canal treating device. In the cordless-type root canal treating device shown in FIG. 9, a battery pack, a micro motor, and a control system corresponding to a control box are incorporated into grip 4 of hand piece 1, and each type of operation units is disposed on a surface of grip 4. Furthermore, in the cordless-type root canal treating device, grip 4 is provided with display unit 16. Therefore, the user can check whether the setting for clockwise rotation or the setting for counterclockwise rotation is applied, without significantly changing a user's line of sight. Although not shown, lead 19 for mouth electrode 19a may be configured to be led from grip 4.

In addition, in root canal treating device 100 according to the first and second embodiments, the case where micro motor 7 is used as a power source for driving cutting tool 5 has been described. The present invention is not, however, limited thereto. Another driving source such as an air turbine may be used.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A dental treating apparatus, comprising:
   a hand piece for drivably holding a cutting tool selected from one of a clockwise cutting tool and a counterclockwise cutting tool, said clockwise cutting tool includes a blade configured to cut when rotated clockwise and said counterclockwise cutting tool includes a blade configured to cut when rotated counterclockwise;
   a power source for driving said cutting tool;
   a driving unit for driving said cutting tool so as to be switchable between first driving in which said cutting tool is driven clockwise as directed toward a tip end of said cutting tool and second driving in which said cutting tool is driven counterclockwise as directed toward the tip end of said cutting tool;
   a controller for, when a rotation direction in which said cutting tool cuts an object to be cut is defined as normal rotation and a rotation direction opposite to said normal rotation is defined as reverse rotation, setting either said first driving or said second driving as driving for said normal rotation, based on said cutting tool being held on said hand piece, wherein
   said controller sets said first driving as the driving for said normal rotation when said clockwise cutting tool is held on said hand piece, and sets said second driving as the driving for said normal rotation when said counterclockwise cutting tool is held on said hand piece;
   a load detecting unit for detecting a load applied to said cutting tool being driven; and
   a determining unit that processes a driving information to determine whether said cutting tool being held on said hand piece is said clockwise cutting tool or said counterclockwise cutting tool by using said load detected by said load detecting unit as said driving information and comparing said load detected by said load detecting unit on said cutting tool generated when said cutting tool is driven with said first driving to cut said object to be cut and said load detected by said load detecting unit on said cutting tool generated when said cutting tool is driven with said second driving to cut said object to be cut.

2. The dental treating apparatus according to claim 1, further comprising:
   a notifier for notifying a user of whether the driving for said normal rotation set by said controller is said first driving or said second driving.

3. The dental treating apparatus according to claim 1, wherein:
   said cutting tool further includes identification information for identifying whether said cutting tool is said clockwise cutting tool or said counterclockwise cutting tool.

4. The dental treating apparatus according to claim 3, wherein:
   said cutting tool has an identification tag or an identification shape for identifying whether said cutting tool is said clockwise cutting tool or said counterclockwise cutting tool, and
   said determining unit is configured to read said identification information from said identification tag or said identification shape to determine whether said cutting tool held on said hand piece is said clockwise cutting tool or said counterclockwise cutting tool, based on said identification information.

5. A dental treating apparatus, comprising:
   a hand piece for drivably holding a cutting tool selected from one of a clockwise cutting tool and a counterclockwise cutting tool, said clockwise cutting tool includes a blade configured to cut when rotated clockwise and said counterclockwise cutting tool includes a blade configured to cut when rotated counterclockwise;
   a power source for driving said cutting tool;
   a driving unit for driving said cutting tool so as to be switchable between first driving in which said cutting tool is driven clockwise as directed toward a tip end of said cutting tool and second driving in which said cutting tool is driven counterclockwise as directed toward the tip end of said cutting tool;
   a controller for, when a rotation direction in which said cutting tool cuts an object to be cut is defined as normal rotation and a rotation direction opposite to said normal rotation is defined as reverse rotation, setting either said first driving or said second driving as driving for said normal rotation, based on said cutting tool held on said handpiece, wherein
   said controller sets said first driving as the driving for said normal rotation when said clockwise cutting tool is held on said hand piece, and sets said second driving as the driving for said normal rotation when said counterclockwise cutting tool is held on said hand piece;
   a root canal length measuring unit for electrically measuring a position of the tip end of said cutting tool in a root canal; and
   a determining unit that determines whether said cutting tool held on said head unit is said clockwise cutting tool or said counterclockwise cutting tool, by using said position of the tip end of said cutting tool measured by said root canal length measuring unit as said driving information and comparing a change in said position when said cutting tool is driven with said first driving and a change in said position when said cutting tool is driven with said second driving.

6. The dental treating apparatus according to claim 2, wherein
   said notifier is a display unit and is provided at said hand piece.

7. The dental treating apparatus according to claim 1, wherein
   said power source is an electrically-driven motor.

8. The dental treating apparatus according to claim 5, further comprising:
   a notifier for notifying a user of whether the driving for said normal rotation set by said controller is said first driving or said second driving.

9. The dental treating apparatus according to claim 8, wherein said notifier is a display unit and is provided at said hand piece.

10. The dental treating apparatus according to claim 5, wherein:
   said cutting tool further includes identification information for identifying whether said cutting tool is said clockwise cutting tool or said counterclockwise cutting tool.

11. The dental treating apparatus according to claim 10, wherein:
   said cutting tool has an identification tag or an identification shape for identifying whether said cutting tool is said clockwise cutting tool or said cutting counterclockwise tool, and
   said determining unit is configured to read said identification information from said identification tag or said identification shape to determine whether said cutting tool held on said head unit is said clockwise cutting tool or said counterclockwise cutting tool, based on said identification information.

12. The dental treating apparatus according to claim 5, wherein said notifier is a display unit and is provided at said hand piece.

* * * * *